United States Patent [19]

Clemence et al.

[11] Patent Number: 4,687,857

[45] Date of Patent: Aug. 18, 1987

[54] ALKYL β-OXO-BENZENEPROPANOATES

[75] Inventors: Francois Clemence; Odile Le Martret, both of Paris, France

[73] Assignee: Roussel Uclaf, Paris, France

[21] Appl. No.: 660,414

[22] Filed: Oct. 12, 1984

[30] Foreign Application Priority Data

Oct. 20, 1983 [FR] France ............... 83 16699

[51] Int. Cl.[4] ............... C07C 101/447; C07D 215/22; C07D 239/22; C07D 277/46
[52] U.S. Cl. .................... 548/195; 544/92; 544/322; 544/329; 544/332; 546/156; 546/308; 546/309; 548/163; 548/185; 548/192; 548/233; 548/236; 548/245; 548/246; 548/251; 548/257; 548/337; 549/69; 560/47
[58] Field of Search ............... 548/163, 185, 192, 195, 548/233, 236, 245, 246, 251, 257, 337; 549/69; 546/156, 309, 308; 560/47; 544/322, 329, 332

[56] References Cited

U.S. PATENT DOCUMENTS

| | | | |
|---|---|---|---|
| 3,798,227 | 3/1974 | Lesher | 546/156 |
| 4,154,756 | 5/1979 | Shepherd | 560/47 |
| 4,397,856 | 8/1983 | Allais et al. | 514/312 |
| 4,486,438 | 12/1984 | Clemmence et al. | 546/156 |

FOREIGN PATENT DOCUMENTS 0040573 11/1981 European Pat. Off. .

OTHER PUBLICATIONS

Mahmoud et al, "Some Reactions with 4H-3,1-Benzoxazin-4-One and Some Studies on the Growth of Bacteria", Rev. Roum. Chim., 1979, 24(6), 849-858, (CA (92):158264y).

Clemence et al., Chemical Abstracts, vol. 105, 226393d (1986).

Primary Examiner—Donald G. Daus
Assistant Examiner—Emily Bernhardt
Attorney, Agent, or Firm—Bierman & Muserlian

[57] ABSTRACT

Novel alkyl β-oxo-benzenepropanoates of the formula

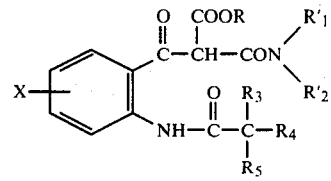

wherein X is in the 5-,6-,7- or 8-position and is selected from the group consisting of hydrogen, halogen, alkyl of 1 to 5 carbon atoms, alkoxy of 1 to 4 carbon atoms, $CF_3-$, $CF_3S-$ and $CF_3O-$, $R_1'$ is selected from the group consisting of hydrogen and alkyl of 1 to 4 carbon atoms, $R_2'$ is selected from the group consisting of hydrogen, thiazolyl, 4,5-dihydrothiazolyl, pyridinyl, oxazolyl, isoxazolyl, imidazolyl, pyrimidyl, tetrazolyl, thienyl, benzothiazolyl and phenyl optionally substituted with at least one member of the group consisting of halogen, alkoxy of 1 to 4 carbon atoms, hydroxy, phenyl, $CF_3-$, $NO_2-$ alkyl of 1 to 4 carbon atoms and alkyl of 1 to 4 carbon atoms substituted with amino, alkylamino or dialkylamino with alkyls of 1 to 3 carbon atoms or $R_1'$ and $R_2'$ taken together with the nitrogen atom to which they are attached form a member of the group consisting of thiazolyl, 4,5-dihydrothiazolyl, pyridinyl, oxazolyl, isoxazolyl, imidazolyl, pyrimidyl, tetrazolyl, thienyl and benzothiazolyl with the double bond being attached to the nitrogen atom, R is alkyl of 1 to 8 carbon atoms, $R_3$ is selected from the group consisting of hydrogen, halogen and alkyl of 1 to 4 carbon atoms, $R_4$ is hydrogen or halogen and $R_5$ is halogen and a process for their preparation and a process for the preparation of compounds of the formula

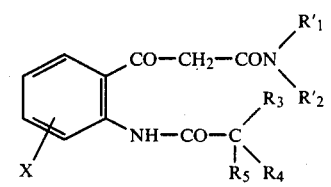

wherein X, $R_1'$, $R_2'$, $R_3$, $R_4$ and $R_5$ have the above definition.

4 Claims, No Drawings

ALKYL β-OXO-BENZENEPROPANOATES

STATE OF THE ART

Published European patent application No. 0040573 which is substantially equivalent to U.S. Pat. No. 4,397,856 describes 3-quinolinecarboxamides substituted in the 2-position of the formula

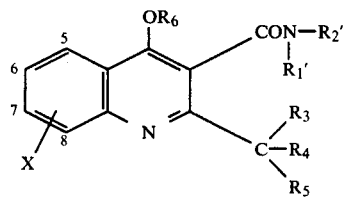

wherein X, $R_1'$, $R_2'$, $R_3$, $R_4$ and $R_5$ have the above definitions and $R_6$ is selected from the group consisting of hydrogen, alkyl of 1 to 8 carbon atoms and acyl of an organic carboxylic acid of 2 to 8 carbon atoms with the proviso that $R_3$, $R_4$ and $R_5$ are not all fluorine at the same time and their addition salts with acids and bases.

The said European application describes several processes for the preparation of the compounds of formula I'. One said process comprises reacting a compound of the formula

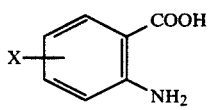

wherein X has the above definition with an acid of the formula

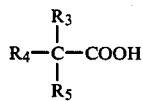

wherein $R_3$, $R_4$ and $R_5$ have the above definition or a functional derivative thereof to obtain a compound of the formula

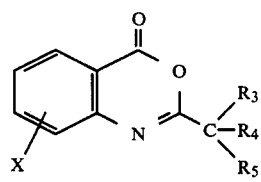

reacting the latter with a compound of the formula

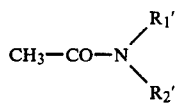

wherein $R_1'$ and $R_2'$ have the above definition to obtain a compound of the formula

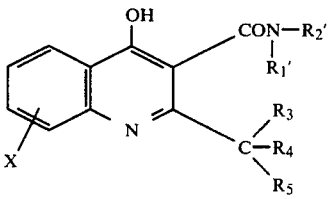

cyclizing the latter in the presence of an alkaline agent to obtain a compound of the formula and optionally subjecting the latter to etherification or esterification to obtain the corresponding compound of formula I' wherein $R_6$ is other than hydrogen and optionally forming a salt thereof with an acid or a base.

However, the said process has several disadvantages. The reaction between the compound of formula VIII and the compound of formula IX takes place in the presence of a strong base which allows the formation of the anion of the compound IX which then reacts on the compound of formula VIII. In particular, such a strong base is an organo-lithium such as n-butyllithium or a lithium amide such as diisopropyllithium amide. However, these reagents present the inconvenience of being costly and have to be handled with care. In fact, the anion formed is very reactive and its reaction on the compound of formula VIII has to be moderated by operating at a low temperature of the order of $-70°$ C. This type of operating condition is not very suitable for the conversion of the process to an industrial scale.

Furthermore, in the case of the compounds of formula IX wherein $R_1'$ is hydrogen, a dianion is formed of the formula $$\overset{\ominus}{C}H_2-\underset{\underset{O}{\|}}{C}-\overset{\ominus}{N}-R_2'$$

The formation of this dianion demands a large quantity of base since it requires two equivalents of the costly reagent.

OBJECTS OF THE INVENTION

It is an object of the invention to find a new synthesis to replace the strong base such as n-butyllithium by a less onerous reagent, of much greater safety in use, which could be employed in smaller quantities, and enabling the cooling at a very low temperature to be eliminated.

It is another object of the invention to provide novel intermediates useful to prepare the compounds of formula I'.

These and other objects and advantages of the invention will become obvious from the following detailed description.

THE INVENTION

The novel intermediates of the invention are alkyl β-oxo-benzenepropanoates of the formula

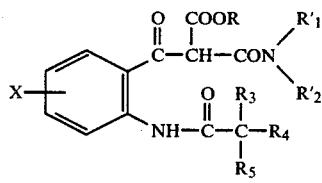

wherein X is the 5-, 6-, 7- or 8-position and is selected from the group consisting of hydrogen, halogen, alkyl of 1 to 5 carbon atoms, alkoxy of 1 to 4 carbon atoms, $CF_3—$, $CF_3S—$ and $CF_3O—$, $R_1'$ is selected from the group consisting of hydrogen and alkyl of 1 to 4 carbon atoms, $R_2'$ is selected from the group consisting of hydrogen, thiazolyl, 4,5-dihydrothiazolyl, pyridinyl, oxazolyl, isoxazolyl, imidazolyl, pyrimidyl, tetrazolyl, thienyl, benzothiazolyl and phenyl optionally substituted with at least one member of the group consisting of halogen, alkoxy of 1 to 4 carbon atoms, hydroxy, phenyl, $CF_3—$, $NO_2—$ alkyl of 1 to 4 carbon atoms and alkyl of 1 to 4 carbon atoms substituted with amino, alkylamino or dialkylamino with alkyls of 1 to 3 carbon atoms or $R_1'$ and $R_2'$ taken together with the nitrogen atom to which they are attached form a member of the group consisting of thiazolyl, 4,5-dihydrothiazolyl, pyridinyl, oxazolyl, isoxazolyl, imidazolyl, pyrimidyl, tetrazolyl, thienyl and benzothiazolyl with the double bond being attached to the nitrogen atom, R is alkyl of 1 to 8 carbon atoms, $R_3$ is selected from the group consisting of hydrogen, halogen and alkyl of 1 to 4 carbon atoms, $R_4$ is hydrogen or halogen and $R_5$ is halogen.

Among the preferred compounds of formula I are those wherein R is methyl, ethyl, n-propyl or isopropyl, those wherein $R_1'$ is hydrogen and those wherein $R_2'$ is thiazolyl.

The novel process for the preparation of the compounds of formula I comprises reacting a compound of the formula

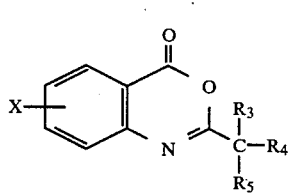

wherein X, $R_3$, $R_4$ and $R_5$ have the above definition with a compound of the formula

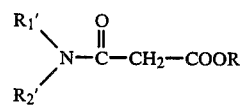

wherein $R_1'$, $R_2'$ and R have the above definition in the presence of a base.

The base reacts with the compound of formula B to form an anion of the formula

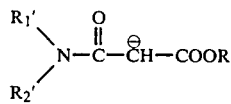

which then reacts with the compound of formula A. The use of the base leads to the formation of a monoanion only, even when $R_1'$ is hydrogen.

Examples of suitable bases are alkali metal hydroxides such as sodium hydroxide, alkali metal hydrides such as sodium hydride and potassium hydride, alkali metal amides such as potassium amide and sodium amide and alkali metal alcoholates such as sodium methylate and potassium butylate and magnesium ethylate. The reaction is effected in the presence of a solvent such as ethyl acetate, dioxane, toluene, dimethylformamide and mixtures thereof, but the preferred solvent is tetrahydrofuran and the preferred reaction temperature is room temperature. The use of two equivalents of the base increases the rate of reaction.

Another process of the invention relates to the preparation of a compound of the formula

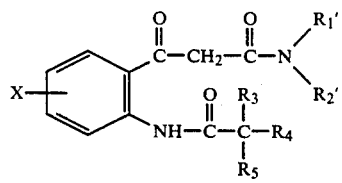

comprising decarbalkoxylating a compound of formula I in an acid medium. Preferably, the decarbalkoxylation is effected by heating in the presence of a mixture of sulfuric acid and dichloroacetic acid. The decarbalkoxylation may also be effected in the presence of trifluoroacetic acid or a mixture of formic acid and methanesulfonic acid or a mixture of acetic acid and sulfuric acid by heating at about 100° C.

The compounds of formula D are intermediates in the process of European patent application No. 0040573 for the formation of 2-substituted-3-quinoline carboxamides of formula I' by cyclization of a compound of formula D in the presence of an akaline agent followed by optional etherification or esterification and optional salification with a base.

The compounds of formula A used as the starting material to prepare the compounds of formula I correspond to the compounds of formula VIII of European application No. 0040573 and the preferred values for X, $R_3$, $R_4$ and $R_5$ are the same as the said application. Compounds of formula A differ from those of formula IX of the said application and the compounds of formula D correspond to the compounds of formula X of the said application.

The process of the present invention has the advantage over EPO application No. 0040573 that the base used for the reaction of compounds of formulae A and B is a weaker base than the prior art base and is easier to use and is cheaper. Moreover, the monoanion formed from the compound of formula B is less reactive than the prior art anion and therefore the reaction does not require the use of very low temperatures or heating of the reaction medium. The lack of cooling makes the reaction easier to control and cheaper.

The preferred base is sodium hydroxide and is used in tetrahydrofuran at room temperature and in comparison with the said prior art process has the advantage of leading to the desired compound without formation by parasitic attack to the 2-carbon atom of the intermediate anion of by products of the formula

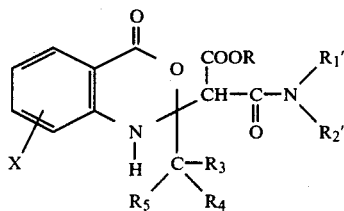

which can not be isomerized to the compounds of formula I. This useless byproduct which is formed in substantial amounts requires an additional separation step.

The decarbalkoxylation step into the compounds of formula D is an additional step but surprisingly the yield of product D is greater than the prior art process.

The compounds of formula D may be used as intermediates in the process of U.S. Pat. No. 4,397,856 to produce 2-substituted-3-quinolinecarboxamides as well as to prepare other 3-quinoline-carboxamides such as those in Belgium Pat. No. 896,941.

In the following examples there are described several preferred embodiments to illustrate the invention. However, it should be understood that the invention is not intended to be limited to the specific embodiments.

EXAMPLE 1

2-(dichloroacetamido)-β-oxo-N-(2-thiazolyl)-(3-trifluoromethyl)-benzene-propanamide

STEP A: Ethyl 2-[(2,2-dichloro-1-oxoethyl)amino]-β-oxo-α-[(2-thiazolylamino)-carbonyl]-3-(trifluoromethyl)-benzene-propanoate 75 ml of tetrahydrofuran and 2.74 g of sodium hydride as a 55% dispersion in oil were mixed together and then at +14° and +15° C., a solution of 12.85 g of ethyl 3-(2-thiazolylamino)-3-oxo-propanoate [described in the Journal Am. Chem. Soc., Vol. 64, 2712.3, (1942)] and 250 ml of tetrahydrofuran were added dropwise. The mixture was cooled to +5° C., and at this temperature a solution of 17.88 g of 2-(dichloromethyl)-8-(trifluoromethyl)-4H-3,1-benzoazine-4-one [prepared as in Example 12 (Stage A) of European Pat. No. 0040573] and 250 ml of tetrahydrofuran were added and after stirring for 15 minutes, the solution was poured into 1 liter of water to which 100 ml of 2N HCl had been added. The mixture was extracted with ether and the organic extracts were dried and evaporated to dryness under reduced pressure. The residue was crystallized from ether, then separated, washed with ether, and dried under reduced pressure to obtain 22 g of ethyl 2-[(2,2-dichloro-1-oxoethyl)amino]-β-oxo-α-[(2-thiazolylamino)-carbonyl]-3-(trifluoromethyl)-benzene-propanoate melting at 180°-182° C.

STEP B: 2-(dichloroacetamido)-β-oxo-N-(2-thiazolyl)-(3-trifluoromethyl)-benzene-propanamide 5.1 g of the product of Step A, 25 ml of pure acetic acid and 0.53 ml of concentrated sulfuric acid were mixed together and heated to 100° C. for 45 minutes until the evolution of gas ceased. 80 ml of water were added to the solution and after separating the organic phase and washing with water and drying under reduced pressure at 100° C., 4 g of 2-(dichloroacetamido)-β-oxo-N-(2-thiazolyl)-(3-trifluoromethyl)-benzene-propanamide melting towards 216°-218° C. were obtained.

EXAMPLE 2

2-(dichloroacetamido)-β-oxo-N-(2-thiazolyl)-(3-trifluoromethyl)-benzene-propanamide

STEP A: Ethyl 2-[(2,2-dichloro-1-oxoethyl)-amino]-β-oxo-α-[(2-thiazolylamino)-carbonyl]-3-(trifluoromethyl)-benzene-propanoate At 20° C., 150 g of 2-dichloromethyl-8-trifluoromethyl-4H-3,1-benzoxazine-4-one, 120 g of ethyl 3-(2-thiazolylamino)-3-oxo-propanoate and 1.5 liters of tetrahydrofuran were mixed together and stirred for 30 minutes and then, while maintaining the temperature at 20° C., 40 g of sodium hydroxide in flakes were added thereto. After stirring the mixture at 20° C. for two hours, it was poured into a mixture of 4.5 liters of water and 150 ml of concentrated hydrochloric acid and the mixture was stirred at 0° to +5° C. for 30 minutes. The crystals formed were separated, rinsed with water and dried to obtain 255 g of ethyl 2-[(2,2-dichloro-1-oxoethyl)-amino]-β-oxo-α-[(2-thiazolylamino)-carbonyl]-3-(trifluoromethyl)-benzene-propanoate melting at 90° C.

STEP B: 2-(dichloroacetamido)-β-oxo-N-(2-thiazolyl)-(3-trifluoromethyl)-benzene-propanamide 100 g of the product of Step A were mixed with 180 ml of dichloroacetic acid with stirring at 20°-25° C. until dissolution and then, at 20°-25° C., 5 ml of concentrated sulfuric acid were added slowly to obtain a solution A.

100 ml of dichloroacetic acid and 5 ml of concentrated sulfuric acid were mixed together and heated to 107° C. Then, under an inert gas, solution A was added slowly, while stirring at 105°-107° C. for 30 minutes. The mixture was then cooled to 20° C. and poured slowly into 2 liters of water. The suspension obtained was stirred at 20° C. for 18 hours, and then the crystals obtained were separated, washed with water and dried to obtain a product identical to that obtained in Example 1.

EXAMPLE 3

2-[(2-chloro-1-oxo-3-methylbutyl)-amino]-β-oxo-N-(2-thiazolyl)-(3-trifluoromethyl)-benzene-propanamide

STEP A: Ethyl 2-[(2-chloro-1-oxo-3-methylbutyl)-amino]-β-oxo-α-[(2-thiazolylamino)-carbonyl]-3-trifluoromethyl-benzene-propanoate Under an inert gas, 5.52 g of sodium hydride dispersed at 55% in oil and 173 ml of tetrahydrofuran were mixed together and then a solution of 26.22 g of ethyl 3-(2-thiazolylamino)-3-oxo-propanoate in 690 ml of tetrahydrofuran was added slowly at 20° C. After stirring for 10 minutes, a solution of 34.5 g of 2-(1-chloro-2-methylpropyl)-8-trifluoromethyl-4H-3,1-benzoxazine-4-one [prepared according to the process described in European Pat. No. 0040573] in 210 ml of tetrahydrofuran was added slowly at 20° C. After stirring at 20° C.

for 35 minutes, the mixture was poured into 200 ml of 2N hydrochloric acid and was extracted with ether. The ethereal phase was washed with water, dried and the solvent was evaporated. The residue was triturated in ether and dried to obtain 42.35 g of ethyl 2-[(2-chloro-1-oxo-3-methylbutyl)-amino]-β-oxo-α-[(2-thiazolylamino)-carbonyl]-3-trifluoromethyl-benzene-propanoate melting at 160° C. A second lot of 8.2 g of the said product was obtained afterwards melting at 160° C.

STEP B:
2-[(2-chloro-1-oxo-3-methylbutyl)-amino]-β-oxo-N-(2-thiazolyl)-(3-trifluoromethyl)-benzene-propanamide 50.4 g of the product of Step A, 252 ml of acetic acid and 5.04 ml of concentrated sulfuric acid were mixed together and the solution was heated at 100° C. for 50 minutes and then, 2 liters of water followed by 500 ml of acetone were added thereto with stirring at 20° C. for 2 hours 30 minutes. A further 1 liter of water was added with stirring for 15 minutes and then the crystals formed were separated and dried to obtain 35 g of 2-[(2-chloro-1-oxo-3-methylbutyl)-amino]-β-oxo-N-(2-thiazolyl)-(3-trifluoromethyl)-benzene-propanamide melting at 186° C.

EXAMPLE 4

2-[(2-chloro-1-oxobutyl)-amino]-β-oxo-N-(2-thiazolyl)-8-trifluoromethyl-benzene-propanamide STEP A: Ethyl 2-[(2-chloro-1-oxobutyl)-amino]-β-oxo-α-[(2-thiazolylamino)-carbonyl]-(3-trifluoromethyl)-benzene-propanoate Under an inert gas, 3.83 g of sodium hydride dispersed at 55% in oil were mixed with 100 ml of tetrahydrofuran and then at 20° C. and with stirring, a solution of 17.92 g of ethyl 3-(2-thiazolylamino)-3-oxo-propanoate in 400 ml of tetrahydrofuran was added slowly. The solution was stirred at 20° C. for 15 minutes and then a solution of 24.4 g of 2-(1-chloropropyl)-8-trifluoromethyl-4H-3,1-benzoxazine-4-one [prepared according to the process described in the Belgian Pat. No. 896,941] in 250 ml of tetrahydrofuran was added thereto. The solution was poured into a mixture of 1 liter of water and 100 ml of 2N hydrochloric acid and was extracted with ether. The ethereal phase was washed with water, dried and the solvent was evaporated. The residue was triturated in ether, and the crystals formed were dried to obtain 34.5 g of ethyl 2-[(2-chloro-1-oxobutyl)-amino]-β-oxo-α-[(2-thiazolylamino)-carbonyl]-(3-trifluoromethyl)-benzene-propanoate melting at 170° C.

STEP B:
2-[(2-chloro-1-oxobutyl)amino]-β-oxo-N-(2-thiazolyl)-8-trifluoromethyl benzene propanamide The product obtained at stage A is mixed with 175 cm³ of acetic acid and 3.5 cm³ of concentrated sulphuric acid is added. The mixture is taken to 100° C. for 45 minutes, then cooled and poured on a mixture of 400 cm³ of water and 40 cm³ of acetone. After agitating for one hour, the crystals formed are separated, washed with water and dried. 22.9 g of the expected product is obtained, m.p. 190° C.

EXAMPLE 5

2-[(2-chloro-1-oxo-3,3-dimethylbutyl)-amino]-β-oxo-N-(2-thiazolyl)-(3-trifluoromethyl)-benzene-propanamide STEP A: Ethyl 2-[(2-chloro-1-oxo-3,3-dimethylbutyl)-amino]-β-oxo-α-[(2-thiazolylamino)-carbonyl]-(3-trifluoromethyl)-benzene-propanoate Using the procedure of Step A of Example 4, 7.7 g of ethyl 3-(2-thiazolylamino)-3-oxo-propanoate and 10.55 g of 2-(1-chloro-2,2-dimethylpropyl)-8-trifluoromethyl-4H-3,1-benzoxazine-4-one [prepared according to the process described in the European Pat. No. 0040573] were reacted to obtain 15.6 g of ethyl 2-[(2-chloro-1-oxo-3,3-dimethylbutyl)-amino]-β-oxo-α-[(2-thiazolylamino)-carbonyl]-3-(trifluoromethyl)-benzene-propanoate melting at 180° C.

STEP B:
2-[2-chloro-1-oxo-3,3-dimethylbutyl)-amino]-β-oxo-N-(2-thiazolyl)-(3-trifluoromethyl)-benzene-propanamide Using the procedure of Step B of Example 4, 14 g of the product of Step A and a mixture of 70 ml of acetic acid and 1.4 ml of concentrated sulfuric acid were reacted to obtain 9.9 g of (2-[2-chloro)-1-oxo-3,3-dimethylbutyl)-amino]-β-oxo-N-(2-thiazoly)-(3-trifluoromethyl)-benzene-propanamide melting at 206° C.

Various modifications of the products and process of the invention may be made without departing from the spirit or scope thereof and it is to be understood that the invention is intended to be limited only as defined in the appended claims.

What we claim is:
1. An alkyl β-oxo-benzenepropanoate of the formula

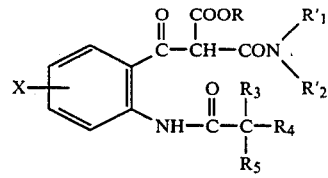

wherein X is in the 5-, 6-, 7- or 8-position and is selected from the group consisting of hydrogen, halogen, alkyl of 1 to 5 carbon atoms, alkoxy of 1 to 4 carbon atoms, $CF_3$—, $CF_3S$— and $CF_3O$—, $R_1'$ is selected from the group consisting of hydrogen and alkyl of 1 to 4 carbon atoms, $R_2'$ is selected from the group consisting of hydrogen, thiazolyl, 4,5-dihydrothiazolyl, pyridinyl, oxazolyl, isoxazolyl, imidazolyl, pyrimidyl, tetrazolyl, thienyl, benzothiazolyl, said heterocycles attached to the nitrogen by a carbon atom and phenyl optionally substituted with at least one member of the group consisting of halogen, alkoxy of 1 to 4 carbon atoms, hydroxy, phenyl, $CF_3$—, $NO_2$—, alkyl of 1 to 4 carbon atoms and alkyl of 1 to 4 carbon atoms substituted with amino, alkylamino or dialkylamino with alkyls of 1·to 3 carbon atoms or $R_1'$ and $R_2'$ taken together with the nitrogen atom to which they are attached form thiazole, R is alkyl of 1 to 8 carbon atoms, $R_3$ is selected from the group consisting of hydrogen, halogen and alkyl of 1 to 4 carbon atoms, $R_4$ is hydrogen or halogen and $R_5$ is halogen.

2. A compound of claim 1 wherein R is selected from the group consisting of methyl, ethyl, n-propyl and isopropyl.

3. A compound of claim 1 wherein $R_1'$ is hydrogen and $R_2'$ is thiazolyl.

4. A compound of claim 2 wherein $R_1'$ is hydrogen and $R_2'$ is thiazolyl.

* * * * *